United States Patent [19]

Erickson

[11] Plant 5,116

[45] Oct. 4, 1983

[54] BUTTERNUT TREE—LOUMIS CULTIVAR

[75] Inventor: William K. Erickson, Bowling Green, Mo.

[73] Assignee: Stark Brothers Nurseries and Orchards Company, Louisiana, Mo.

[21] Appl. No.: 345,098

[22] Filed: Feb. 2, 1982

[51] Int. Cl.[3] ..... A01H 5/03

[52] U.S. Cl. ..... Plt./30

[58] Field of Search ..... Plt./30

*Primary Examiner*—Robert E. Bagwill

*Attorney, Agent, or Firm*—Burns, Doane, Swecker & Mathis

[57] ABSTRACT

A new and distinct variety of Butternut tree (i.e. *Juglans cinerea*) is provided which originated as a chance seedling among seedlings produced from seed planted in a cultivated area. The new variety is of unknown parentage and readily can be distinguished by its ability to form large quantities of nuts which are frequently borne in clusters of five or more. Unlike nuts commonly formed on Butternut trees, the nuts of the present variety have the ability to readily separate from the hull. Additionally, the trees of the present variety exhibit good winter hardiness and resistance to the Witches'-Broom disease which commonly afflicts Butternut trees.

2 Drawing Figures

SUMMARY OF THE INVENTION

The new variety of Butternut tree described herein resulted from seed planted by me during 1969 in my orchard at Route 2, Bowling Green, Pike County, Mo. The parentage of the new variety is unknown. The seed germinated in 1970 and the resulting trees fruited during 1973. Observation of the resulting trees over the succeeding five year period led to the selection of the new variety. Since common Butternut trees bloom relatively early and before most Black Walnut trees, the flowers are frequently damaged by low temperatures. Accordingly, most Butternut trees are frequently of relatively low productivity. I was particularly impressed by the tree of the new variety because of its great productivity and its ability to withstand low temperatures. Additionally, the tree of the new variety unlike other Butternut trees in the vicinity, appeared to be free from the Witches'-Broom disease which has been a major cause for the decline of native Butternut tree plantings. The new variety was first asexually reproduced during 1978 by grafting following five years of observation.

The new variety was observed to possess the following combination of characteristics:

(a) the formation of a large tree of medium vigor, (b) extremely high nut productivity wherein average sized nuts are frequently borne in clusters of approximately five or more, (c) the propensity for the nuts to readily separate from the hull when opened, (d) the formation of buds which exhibit good winter hardiness, (e) the formation of flowers which exhibit good resistance to frost, (f) the relative absence of damage by casebearer insects, and (g) resistance to Witches'-Broom disease.

It was found that the blooming period for male and female flowers of the new variety overlap nicely. The pistillate flowers set nuts even if low temperatures are encountered in the Spring and form considerably more nuts than the Chamberlain variety and all other Butternut seedlings I have observed. For instance, I have observed the Chamberlain variety to produce singly borne nuts or clusters of up to about three nuts. However, the present Butternut variety frequently produces nuts in numerous clusters of approximately five to ten nuts per cluster. The appearance and size of the individual nuts of the present variety are substantially identical to that of other Butternut varieties. The nut hulls of the present variety start dropping in late August and finish dropping during late September when grown at Bowling Green, Mo.

Asexual reproduction of the new variety by grafting has confirmed that its characteristics come true to form and are established and transmitted through succeeding generations.

The new variety has been named the Loumis cultivar.

The specimens described herein were grown and observed near Bowling Green, Mo.

BRIEF DESCRIPTION OF THE PHOTOGRAPHS

The accompanying photographs show typical specimens of the new variety as depicted in color as nearly true as it is reasonably possible to make the same in color illustrations of this character while grown near Bowling Green, Mo.

DETAILED DESCRIPTION OF NEW VARIETY

Figure 1:
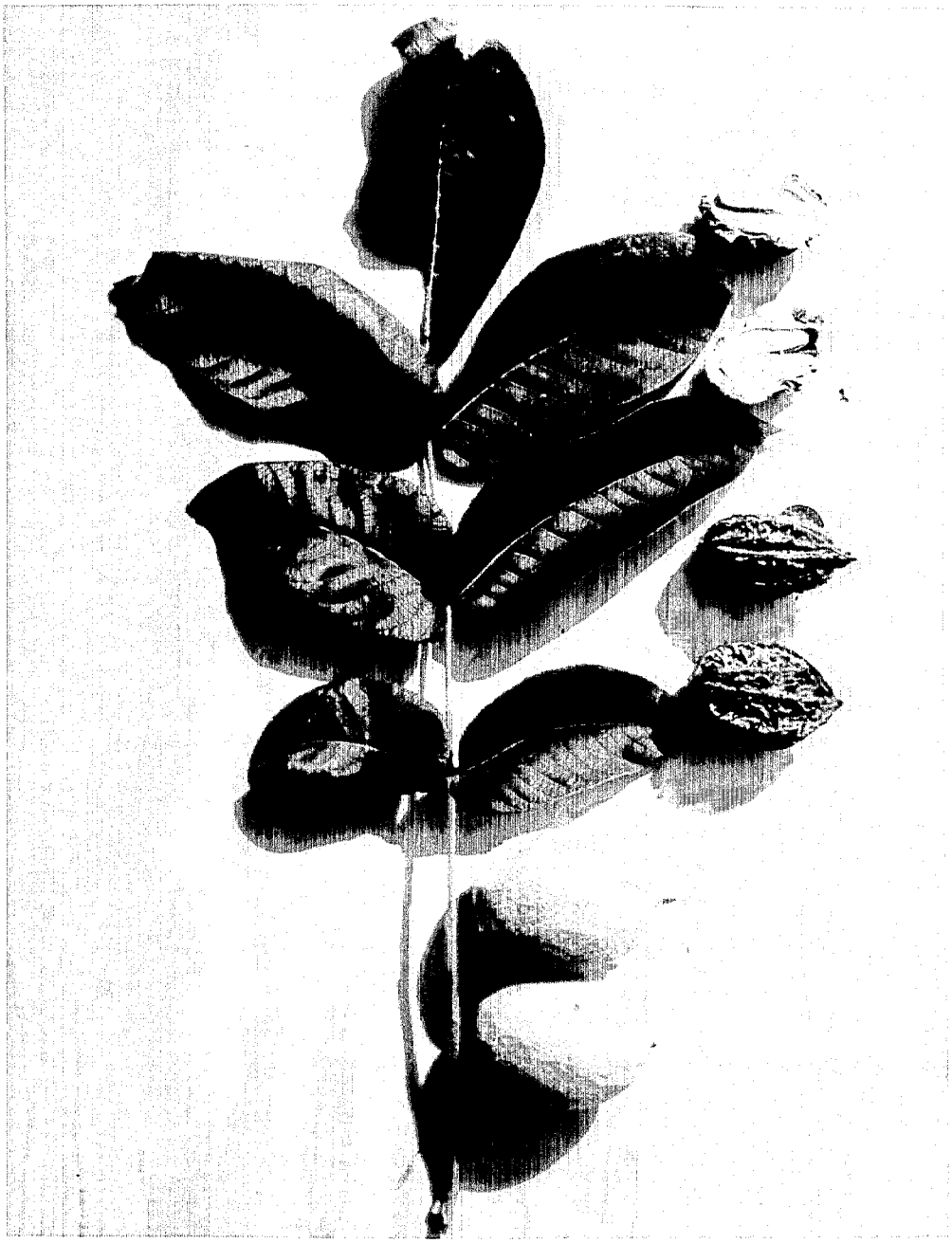
FIG. 1 illustrates typical foliage, nuts in the hull, whole nuts out of the hull, and nuts while halved. Some of the leaflets evidence insect damage.
Figure 2:
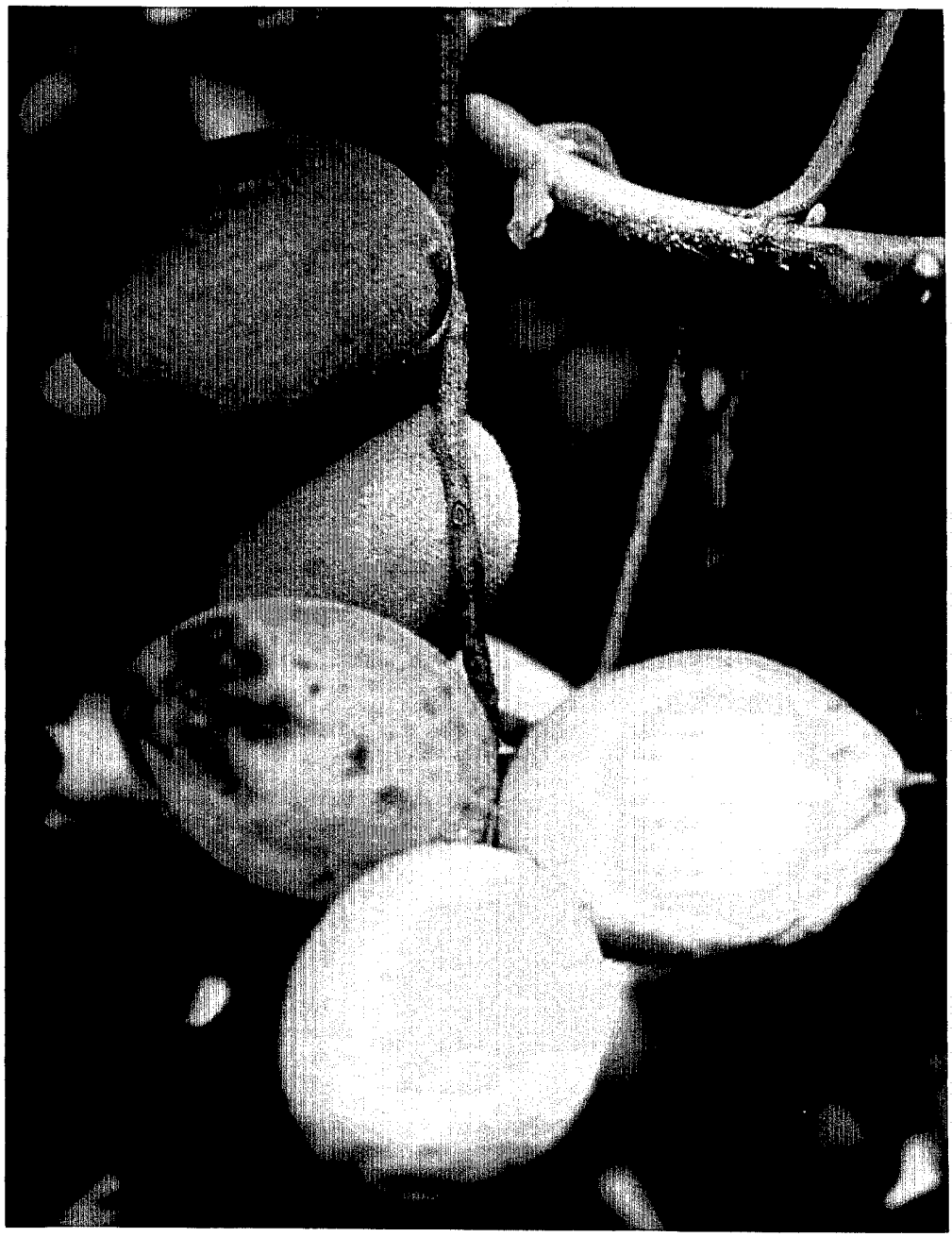
FIG. 2 illustrates a typical cluster of five nuts of the new variety while in the hull and still borne on the tree.

Dates of first and last harvest: August 25 and September 25.

Tree: Large size, hardy, very productive, medium vigor, slim configuration.

*Trunk.*—The bark is lighter, grayer, and much smoother than that of the common Black Walnut, and the heartwood is light chestnut in coloration.

*Twigs.*—Covered with reddish brown to reddish gray pubescence.

*Foliage.*—Moderately sparse, lanceolate, pointed, compound composed of approximately 7 to 11 leaflets oppositely arranged on petiole, underside covered with reddish brown to reddish gray pubescence. Leaflet length. — Approximately 5 to 6 inches. Leaflet width. — Approximately 2½ to 3 inches. Color. — Forest Green — Plate XVII 29GG-Y-m Ridgeway's Color Standards. Margin. — Serrated. Petiole. — Covered with reddish brown to reddish gray pubescence.

Flowers: Both male and female flowers are on same tree as other *Juglans cinerea,* the male flowering structure is a catkin approximately three to five inches long with staminate flowers and the female flowering structure is a raceme of approximately three inches with small inconspicuous pistillate flowers.

Nuts: Abundant, uneven, semi-free, frequently borne in clusters of approximately 5 to 10 nuts per cluster.

*Time of harvesting.*—August 25 to September 25 at Bowling Green, Mo.

*Size.*—Approximately 2½ to 2⅝ inches in length and approximately 1¾ to 1⅞ inches in width.

*Weight.*—Approximately 12 to 15 grams per nut, approximately 30 to 38 nuts per pound, approximately 25 percent by weight of the nut is kernel.

*Shape.*—Round, mucronate.

*Shell.*—Thick, medium hard, is easily removed from the hull or husk, is capable of being halved.

*Color.*—Bone Brown — Plate XL 13-O-Y-O-m Ridgeway's Color Standards.

*Kernel.*—Flavor is good and is milder than other Butternuts, sutures are uneven, and the texture is crunchy and fine grained.

Hardiness: Very good.

Use: Market.

Resistance to insects: Good, there is a relative absence of damage by casebearer insects.

Resistance to diseases: Appears to be resistant to Witches'-Broom disease which commonly afflicts Butternut trees, and appears to also be free of walnut anthracnose.

I claim:

1. A new and distinct variety of *Juglans cinerea,* substantially as illustrated and described, characterized by (a) the formation of a large tree of medium vigor, (b) extremely high nut productivity wherein average sized nuts are frequently borne in clusters of approximately five or more, (c) the propensity for the nuts to readily separate from the hull when opened, (d) the formation of buds which exhibit good winter hardiness, (e) the formation of flowers which exhibit good resistance to frost, (f) the relative absence of damage by casebearer insects, and (g) resistance to Witches'-Broom disease.

* * * * *